US00PP30619P2

(12) United States Plant Patent
Kleinwee

(10) Patent No.: US PP30,619 P2
(45) Date of Patent: Jun. 25, 2019

(54) ***LOBELIA* PLANT NAMED 'LOBZ0014'**

(50) Latin Name: *Lobelia erinus*
Varietal Denomination: LOBZ0014

(71) Applicant: SYNGENTA PARTICIPATIONS AG, Basel (CH)

(72) Inventor: Theodorus Cornelis Maria van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,671

(22) Filed: Apr. 5, 2018

(30) Foreign Application Priority Data

Dec. 22, 2017 (QZ) ..... PBR 2017/3387

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./451
See application file for complete search history.

*Primary Examiner* — Susan McCormick Ewoldt
(74) *Attorney, Agent, or Firm* — Dale Skalla

(57) ABSTRACT

A new *Lobelia* plant named 'LOBZ0014' particularly distinguished by its relatively large, violet-blue flowers, medium green foliage, very good branching and a mounding to semi-trailing plant habit.

1 Drawing Sheet

Latin name of the genus and species of the plant claimed: *Lobelia erinus.*

Varietal denomination: 'LOBZ0014'.

BACKGROUND OF THE NEW PLANT

The present invention comprises a new and distinct cultivar of *Lobelia*, botanically known as *Lobelia erinus* and hereinafter referred to by the cultivar name 'LOBZ0014'.

'LOBZ0014' is a product of a planned breeding program. The new cultivar has relatively large, violet-blue flowers, medium green foliage, very good branching and a mounding to semi-trailing plant habit.

The seed from which the variety was grown originates from an open pollination made on the open field in the summer of 2012 in The Netherlands.

The female parent was an unpatented, proprietary *Lobelia* plant designated 'LOB11-885-1', having smaller flowers, a more violet flower colour and a more compact growing habit than 'LOB0014'.

The male parent of 'LOBZ0014' is unknown, as the cross from which the variety originates was an open pollination.

The resulting seeds were sown in May 2013 and 'LOBZ0014' was selected as one flowering plant within the progeny of the stated cross in September 2013 in a controlled environment in Andijk, The Netherlands.

The first act of asexual reproduction of 'LOBZ0014' was accomplished when vegetative cuttings were propagated from the initial selection in the fall of 2013 in a controlled environment in Andijk, The Netherlands.

BRIEF SUMMARY OF THE INVENTION

Horticultural examination of plants grown from cuttings of the plant initiated in the spring of 2014 in Andijk, The Netherlands, and continuing thereafter, has demonstrated that the combination of characteristics as herein disclosed for 'LOBZ0014' are firmly fixed and are retained through successive generations of asexual reproduction.

'LOBZ0014' has not been observed under all possible environmental conditions. The phenotype may vary significantly with variations in environment such as temperature, light intensity and day length.

A Plant Breeder's Right for this cultivar was applied for in the European Union on Dec. 22, 2017, No. 2017/3387. 'LOBZ0014' has not been made publicly available prior to the effective filing date of this application, notwithstanding any disclosure that may have been made less than one year prior to the effective filing date of this application by the inventor or another who obtained 'LOBZ0014' directly from the inventor.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

The accompanying photograph drawings show typical flower and foliage characteristics of 'LOBZ0014' with colors being as true as possible with an illustration of this type.

Figure 1:
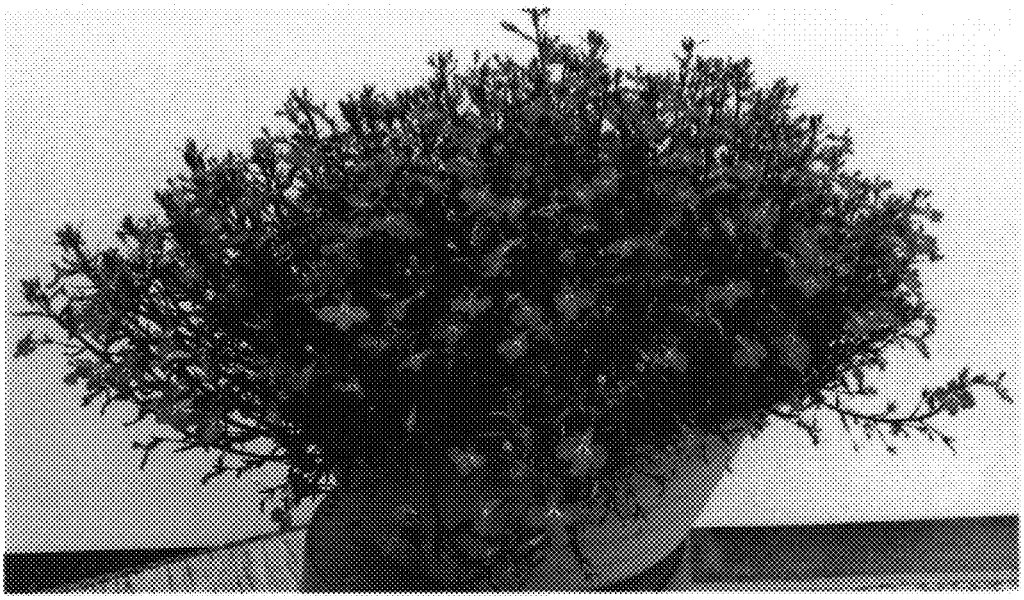
Figure 2:
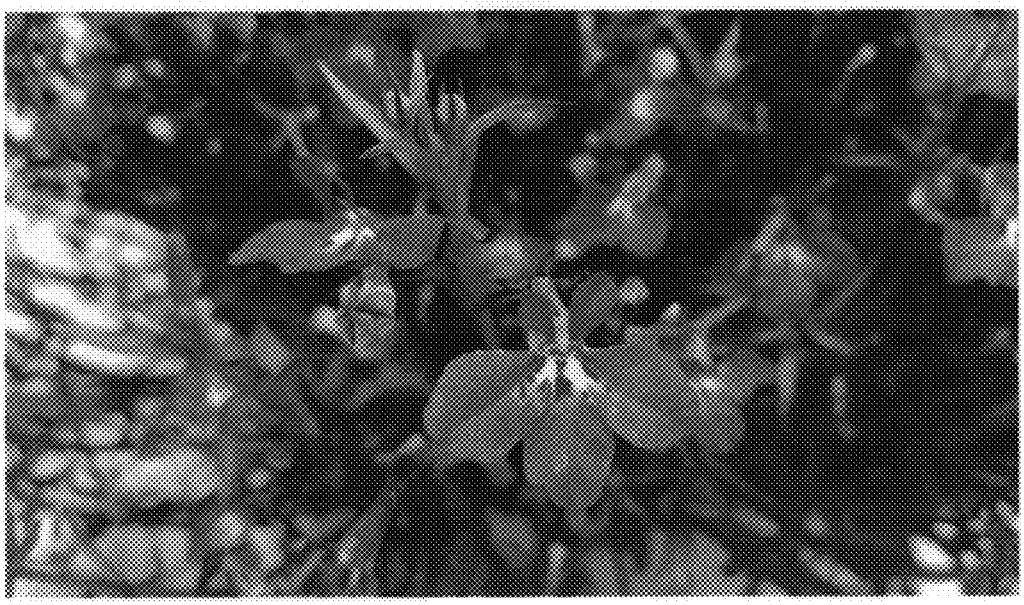

The drawings show in FIG. 1 a flowering potted plant of the new variety and in FIG. 2 a close-up of its flowers.

DETAILED BOTANICAL DESCRIPTION

The aforementioned photographs were taken in September 2017 from plants grown in an outdoor trial in Andijk, The Netherlands. These plants were grown in containers and were approximately 17 weeks of age. The close-up photograph was taken at the same time.

The measurements were taken in Andijk, The Netherlands in September 2017 on 17 week old plants that were grown outside in containers. Culture of these plants had started in week 21, 2017 with planting of rooted, non pinched cuttings.

Color chart used: The Royal Horticultural Society Colour Chart (R.H.S.), 2001.

TABLE 1

DIFFERENCES BETWEEN THE NEW VARIETY 'LOBZ0014' AND A SIMILAR VARIETY

| | 'LOBZ0014' | Techno Violet C0973-3 (LOBMOUNLILA) U.S. Plant Pat. No. 18,410 |
|---|---|---|
| Flower color: | Violet blue | Light Violet |
| Flower, diameter: | Relatively large | Relatively small |
| Plant habit | Mounding to semi-trailing | Trailing |

Plant:

*Growth and habit*.—Rather vigorous; dense and freely branched with short internodes, mounding to semi trailing plant habit.

*Height*.—About 15 cm.

*Height* (*inflorescence included*).—33 cm.

*Width*.—50 cm.

*Branching characteristics*.—6 main stems, each with 3 to 4 secondary branches.

*Crop time to flowering, resp*.—Time to produce a finished flowering plant: About 12 weeks for a 12 cm pot.

*Garden performance*.—Used as patio planters, in mixed container plantings, or in garden beds.

*Time to initiate and develop roots*.—14-20 days at 22° C.

*Root description*.—Fibrous and freely branching.

Stem:

*Characteristics*.—With slightly strengthened, protruding edges, side branches are developed at almost every node.

*Stem length*.—Between 12-25 cm.

*Diameter*.—0.2-0.4 cm.

*Internode length*.—2.0-4.5 cm.

*Color*.—Mainly RHS 138A.

*Texture*.—Pubescent.

Foliage:

*Arrangement*.—Alternate.

*Shape*.—Oblanceolate, more lanceolate at top of leaf.

*Apex*.—Lorate.

*Base*.—Decurrent.

*Margin*.—Entire to slightly incised.

*Leaf length*.—2.5-3.3 cm.

*Leaf width*.—0.4-0.9 cm.

*Immature leaf, color upper surface*.—RHS 137A.

*Immature leaf, color lower surface*.—RHS 138B.

*Mature color upper surface*.—RHS 146A.

*Mature color lower surface*.—RHS 147C.

*Venation type*.—Pinnate.

*Venation color, upper surface*.—RHS 146A.

*Venation color, lower surface*.—RHS 147C.

*Texture*.—Short hairs on both surfaces.

*Petiole*.—No petiole, leaves are sessile.

Inflorescence:

*Type of inflorescence*.—Raceme, composed of single flowers in an alternate arrangement with one flower per node, subtended by a small leaflet.

*Blooming habit*.—Continuous through the growing season from spring to the fall.

*Quantity of inflorescences per plant*.—About 200.

*Quantity of flowers per inflorescence*.—Up to 17 open flowers, and additional buds.

*Lastingness of individual blooms on the plant*.—3-6 days, depending on temperature.

*Fragrance*.—None.

*Inflorescence length*.—About 10 cm.

Peduncle:

*Color*.—RHS 143A-RHS 144A.

*Length*.—Up to 15 cm.

*Diameter*.—0.2 cm.

*Texture*.—Pubescent.

Pedicels:

*Color*.—Upper side: RHS 146A, lower side: RHS 146C.

*Length*.—2.0-2.7 cm.

*Diameter*.—0.1 cm.

*Texture*.—Pubescent.

Flower:

*Corolla type and shape*.—Single, zygomorphic; upper lip is formed by two small petals, lower lip has three larger petals; petals are fused at the base forming a relatively long funnel-shaped tube.

Immature flower:

*Main color upper surface*.—RHS N88A and at base N82B.

*Main color lower surface*.—RHS N82B at top, RHS 84D at the base.

*Immature flower, width*.—0.9 cm.

Mature flower:

*Flower*, (*horizontal*) *length*.—2.3 cm.

*Flower*, (*horizontal*) *width*.—2.6 cm.

*Flower*, *vertical length* (*depth*).—2.0 cm.

*Color upper lip, upper surface*.—RHS 93B, RHS 94C at base.

*Color upper lip, lower surface*.—RHS 91B, RHS 91D at base.

*Upper petal lobes, length* (*from the tube opening*).—1 cm.

*Upper petal lobes, width*.—0.3 cm.

*Color lower lip, upper surface*.—RHS 93B.

*Color lower lip, lower surface*.—RHS 91A.

*Nectaries at base of lower petals*.—RHS 93B.

*Lower petal lobes, length* (*from the corolla opening*).—0.6 cm.

*Lower petal lobes, width*.—0.15 cm.

*Tube, color* (*outside*).—RHS 77A.

*Tube length*.—0.9-1 cm.

*Tube width*.—0.3-0.4 cm.

Petal (lobes):

*Shape*.—Obovate.

*Apex*.—Mucronulate.

*Base*.—Fused.

*Margin*.—Entire.

*Texture upper surface*.—Glabrous.

*Texture lower surface*.—Short hair, mainly along the mid vein.

Flower bud:

*Shape*.—Gibbous.

*Length*.—0.6 cm.

*Diameter*.—0.4 cm.

*Color* (*at tight bud*).—Part is RHS 155A, up to a bit greenish.

Calyx:

*Shape.*—5 sepals in a whorl, slanting outwards, bases fused.

*Sepal color.*—RHS 187A, very dark.

*Sepal length* (*fee ends*).—0.9 cm.

*Width.*—0.1 cm, 2 mm wider towards top.

*Shape.*—Ligulate.

*Apex.*—Acute.

*Base.*—Fused.

*Texture.*—Pubescent.

Reproductive organs:

Stamens:

*Quantity.*—5.

*Filament, color.*—RHS N81A.

*Filament length.*—0.6 cm.

*Filament, diameter.*—0.1 cm.

*Anther color.*—RHS 202A to B some spots RHS N79.

*Anther length.*—0.2 cm.

*Pollen amount.*—Abundant

*Pollen color.*—RHS 3C.

Pistil:

*Quantity per flower.*—1.

*Length.*—0.7 cm.

*Stigma color.*—RHS 147A.

*Stigma length.*—0.2 cm.

*Style color.*—RHS 19C.

*Style length.*—0.6-0.8 cm.

Fruit and seed set: Yes, some seed development observed in the trial fields.

Disease and insect resistance: Resistance and susceptibility typical for the species, no special observations made.

What is claimed is:

1. A new and distinct cultivar of *Lobelia* plant named 'LOBZ0014' substantially as illustrated and described herein.

* * * * *